US009675717B2

(12) United States Patent
Kim et al.

(10) Patent No.: US 9,675,717 B2
(45) Date of Patent: Jun. 13, 2017

(54) ELECTROMAGNETIC POLYMER COMPOSITE MATERIAL FOR ANTI-FOULING EFFECT

(71) Applicant: The University of Toledo, Toledo, OH (US)

(72) Inventors: Dong-Shik Kim, Sylvania, OH (US); Youngwoo Seo, Toledo, OH (US)

(73) Assignee: The University of Toledo, Toldeo, OH (US)

( * ) Notice: Subject to any disclaimer, the term of this patent is extended or adjusted under 35 U.S.C. 154(b) by 396 days.

(21) Appl. No.: 14/291,795

(22) Filed: May 30, 2014

(65) Prior Publication Data

US 2014/0356228 A1 Dec. 4, 2014

Related U.S. Application Data

(60) Provisional application No. 61/829,527, filed on May 31, 2013.

(51) Int. Cl.
*H01B 1/20* (2006.01)
*C09D 5/23* (2006.01)
(Continued)

(52) U.S. Cl.
CPC .......... *A61L 2/03* (2013.01); *C09D 5/16* (2013.01); *C09D 5/1687* (2013.01); *C09D 5/23* (2013.01);
(Continued)

(58) Field of Classification Search
CPC ... H01B 1/00; H01B 1/12; H01B 1/22; H01B 1/24; C09D 5/16; C09D 5/1606;
(Continued)

(56) References Cited

U.S. PATENT DOCUMENTS 5,532,025 A * 7/1996 Kinlen ............... B05D 7/14
106/14.34
6,048,920 A * 4/2000 Ziolo ............... B82Y 25/00
252/62.54

(Continued)

OTHER PUBLICATIONS

Ikeda et al "Enzymatic sunthesis and curing of poly(cardanol)", Polymer Journal, vol. 32, No. 7, pp. 589-593 (2000).*

*Primary Examiner* — Mark Kopec
(74) *Attorney, Agent, or Firm* — Emch, Schaffer, Schaub & Porcello Co., L.P.A.

(57) ABSTRACT

The antifouling coating is a composite material consisting of fluorinated electroactive bipolymers and magnetic particles. This composite material is coated on a solid surface to make a smooth durable grassy coating. The coating generates electrical current when an electrolytic liquid flows over it, which prevents bacterial cells from attaching to the surface. It prevents virus and protein attachment. It also prevents chemical corrosion of a surface. The composite material itself, and the antifouling method that uses fluoride compounds and electrical current that is generated by the fluid flow are disclosed for a patent. The composite material can be applied to medical devices, biomedical devices, industrial equipment, ship's hulls, food processing equipment, food processors, drinking water distribution systems, and home electrical appliances.

15 Claims, 7 Drawing Sheets

(51) Int. Cl.
*A61L 2/03* (2006.01)
*C09D 5/16* (2006.01)
*C09D 5/24* (2006.01)
*C09D 7/12* (2006.01)
*C08K 3/22* (2006.01)

(52) U.S. Cl.
CPC ............ *C09D 5/24* (2013.01); *C09D 7/1216* (2013.01); *H01B 1/20* (2013.01); *C08K 2003/2265* (2013.01)

(58) Field of Classification Search
CPC ...... C09D 5/1637; C09D 5/1687; C09D 5/23; C08K 5/13; C08K 5/138
See application file for complete search history.

(56) References Cited

U.S. PATENT DOCUMENTS

| | | | |
|---|---|---|---|
| 8,299,199 B2 * | 10/2012 | Dai | C07F 7/0852 528/25 |
| 8,575,231 B2 * | 11/2013 | Dahling | C08G 18/4238 523/122 |
| 9,045,651 B2 * | 6/2015 | Chen | C08F 220/06 |

* cited by examiner

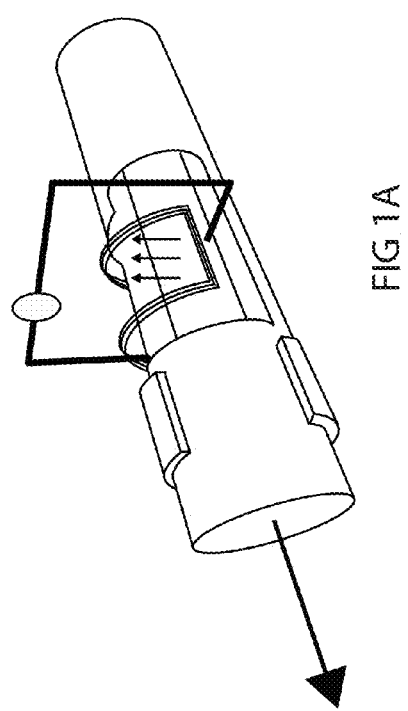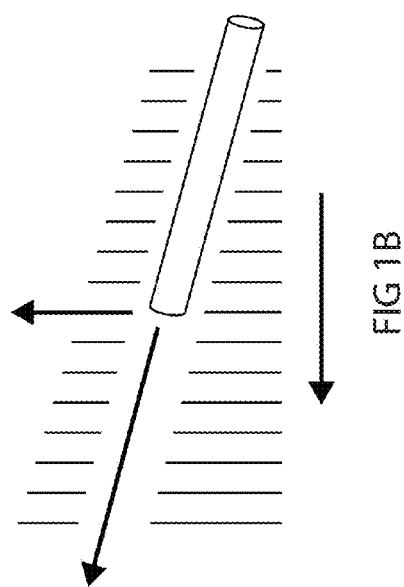
FIG 1A
FIG 1B

ELECTROMAGNETIC POLYMER COMPOSITE MATERIAL FOR ANTI-FOULING EFFECT

CROSS REFERENCE TO RELATED APPLICATIONS

This application claims the benefit of U.S. provisional patent application Ser. No. 61/829,527 and filed on May 31, 2013.

GOVERNMENT LICENSE RIGHTS

This invention was made with government support under CBET-0933288 awarded by NSF. The government has certain rights in the invention.

TECHNICAL FIELD

The present disclosure relates to the field of antifouling agents.

BACKGROUND OF THE INVENTION

Bacterial fouling (biofouling in short, hereafter) is a serious problem in every aspect of our lives. Bacterial attachment to solid surfaces and colonization is the main source of bacterial infection. Medical devices, biomedical equipment, food packaging, and drinking water distribution systems are all susceptible to biofouling and pose potentially harmful impacts on human health. For example, urinary tract infection is the most common hospital associated infection and 80% are caused by biofouling in an indwelling urinary tract catheter. Another example is the biofouling on ships' hulls that is a primary cause of attachment of sea creatures, such as barnacles, algae, mussels, and shells, resulting in higher friction on the hulls. As a result, 30-50% more energy is consumed during sailing.

One of the methods to address this biofouling problem is to use antibiotic or bactericidal agents. In this method, antibiotic materials are either impregnated inside the wall of solid surface to be protected from bacterial colonization, or coated on the surface of it to prevent biofouling. In this case, antifouling agents diffuse out of the surface as they dissolve into the water and kill the bacteria near the surface. Many antifouling systems in current health-care products, water filtration, home appliances such as air conditioners, humidifiers, and air purifiers, and kitchen appliances are based on the diffusion of antibiotic (or bactericidal) agents from the contact surface. The biggest problem in this method is the rapid depletion of the antibiotic agent as it diffuses out and is removed from the surface. Besides, these antibiotic chemicals may be harmful to humans and environment. Furthermore, there are reports that bacteria develop antibiotic resistance to these chemicals. Common diffusion-based agents currently used in the market are triclosan, triclocarban, Trichlorocarbamidem, chloroxylenol, nitrofurazone and organic silver. Silver coating is gaining much attention as an alternative to traditional bactericides. Again, the coating loses its effect in a short time period. Silver coatings are expensive, and their antifouling effect is controversial. In one study, silver-impregnated catheters were associated with more frequent bacteriuria and an increased risk of staphylococcal bacteriuria. Conclusively silver coatings may diminish bacteriuria for a few days but are costly and have no role in long-term prevention.

There are non-diffusion-based antifouling methods that use surface structure modifications with various polymeric materials. Chemicals that are being used or investigated are polyethylene glycol, poly(2-hydroxyethyl methacrylate), i.e., PHEMA, and furanones. Although these materials last longer on solid surfaces than the diffusion-based agents, their efficacies are not sufficient to outweigh their costs. For example, to form PHEMA brushes on a solid surface, atom transfer radical polymerization has to be performed on the silanized surface. This type of coating process is not simple, and costly. Further, there remains uncertainty of the coating's mechanical durability and its effectiveness in preventing biofouling.

In another category of antifouling strategies, there are physical methods that use sonication, UV light, and electrical pulse. These methods are more effective in removing the bacterial colonies already formed on the surface rather than preventing the cell attachment. However, these physical methods have many limitations that overshadow their efficacy and durability. The bacteria contaminated area that sonication and UV light can be applied is limited because ultrasound and UV light can only be applied to a small area with a short penetration depth. They are inconvenient to use due to accompanying auxiliary devices such as sonnicator, UV generator, batteries, etc. Moreover, in the case of using them inside human body, it is highly suspected they may be harmful to human body cells. Periodic electrical pulse was reported effective in preventing biofouling and also effective to remove already formed biofilms. Electric pulse only travels through conductive materials and this requirement also restricts its application as well as other requirements such as a pulse generator, controller, and batteries.

The present invention is based on the effect of electrical current on preventing bacterial adhesion. As demonstrated in electrical pulse generators, applying electrical current to the surface of concern is regarded a plausible way to protect the surface from biofouling. Because the electrical current is generated by the movement of fluid over the surface of the coating agent, it does not require a pulse generator, batteries, or any other auxiliary devices. Because it consists of cross-linked polymers and magnetic particles, it forms a durable coating that lasts a very long time. This coating has another potential advantage that protects surfaces from chemical corrosion.

SUMMARY OF THE INVENTION

Disclosed herein is an antifouling agent for protecting a solid surface from bacterial fouling. The antifouling composite or agent consists of fluorinated electroactive polymers and magnetic particles. When polymerized and cross-linked on a solid surface, these agents form a smooth durable coating. When there is a flow of electrolytic liquid over the coating, an electrical current is generated through Fleming's right hand rule. The electrical current on the solid surface effectively prevents bacterial adhesion.

The antifouling agent disclosed herein can be applied to any solid surfaces and can easily form a durable coating.

The antifouling agent disclosed herein can be adapted to prevention of protein adsorption and surface corrosion.

Further disclosed herein is a method of making a fluorinated polycardanol electromagnetic coating material. The method comprises of basic materials, polymerization procedure, and coating procedure.

BRIEF DESCRIPTION OF THE DRAWINGS

FIGS. 1A and 1B are perspective schematic views of the flow induced voltage.

DETAILED DESCRIPTION OF THE INVENTION

Figure 2:
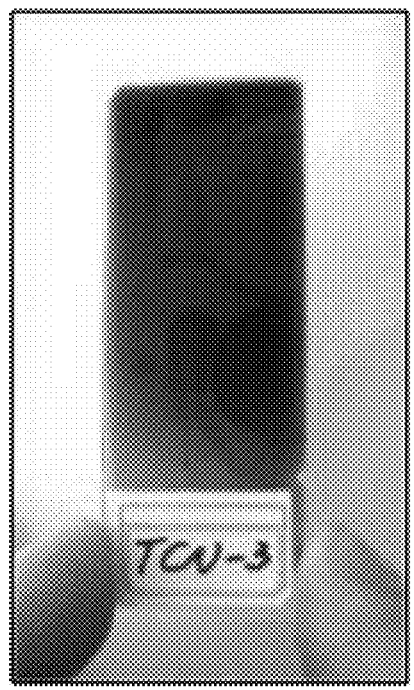
FIG. 2 is a photograph of the plastic slide coated with the antifouling composite agent.
Figure 3:
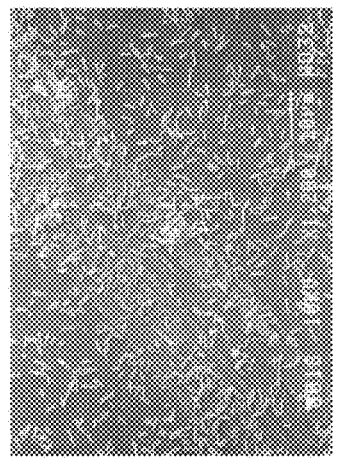
FIG. 3 shows scanned images from fluorescent microscope of bacterial cells and colonies on (a) a regular plastic surface and (b) a plastic surface coated with the antifouling composite agent.
Figure 3:
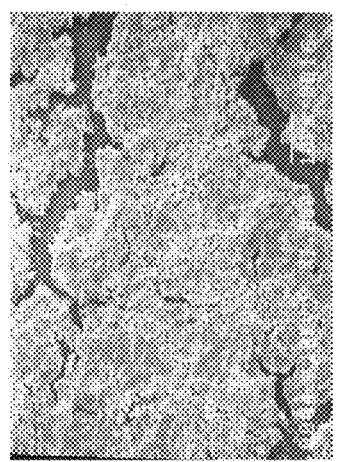

Throughout the entire specification, including the claims, the word "comprise" and variations of the word, such as "comprising" and "comprises" as well as "consists," "having," "includes," and "including," and variations thereof, means that the named steps, elements or materials to which it refers are essential, but other steps, elements, or materials may be added and still form a construct within the scope of the claim or disclosure. When recited in describing the invention and in a claim, it means that the invention and what is claimed is considered to be what follows and potentially more. These tears, particularly when applied to claims, are inclusive or open-ended and do not exclude additional, unrecited elements or method steps.

Various embodiments are described herein in the context of apparatus, method, system, and/or process for the antifouling agent and antifouling coating. Those of ordinary skill in the art will realize that the following detailed description of the embodiments is illustrative only and not intended to be in any way limiting. Other embodiments will ready suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skill in the art having the benefit of this disclosure.

The term "composite" as used herein refers to a gelatinous material that is synthesized by combining electroactive polymers, fluoride compound, and magnetic particles to install antifouling activity. The electroactive polymers naturally have antifouling effects and with fluorination, they show enhanced antifouling effects. Fluoride compounds in the line of methacrylate compounds with 10-20 fluoride molecules are preferred for the radical polymerization with polycardanol. Addition of the electrical current generated by the combinational effect of the electrolyte flow and electromagnetic field, its antifouling effect is much more enhanced.

The term "electroactive polymers" as used herein refers to any biopolymer materials that have electrical conductivity or redox potential. Examples are some natural polyphenols and polyaniline.

Natural biopolymers can be extracted from their resources according to proper extraction methods. Polyaniline can be synthesized using aniline monomers according to proper polymerization methods.

The antifouling agent described herein can be applied to any solid surface. The surface can be coated by dipping method, spin coating method, or spray.

The antifouling composite agent can be used to prevent the adhesion of bacterial cells, viruses, and proteins. In some embodiments, the antifouling agent can be used for surface corrosion prevention.

The antifouling composite agent, a fluorinated polycardanol and ferrite compound known as Flow Induced Electromagnetic Field (FI-EMF), prevents or delays initial cell attachment on the surface. It does not necessary kill the cells. By preventing and reducing the initial attachment, the solid surface can maintain sterile conditions. The FI-EMF may be coated on a solid surface to make a smooth, durable, glassy coating. The coating generates electrical current when an electrolytic liquid flows over it, which prevents bacterial cells from attaching to the surface. It prevents virus and protein attachment. It also prevents chemical corrosion of a surface. The antifouling composite agent itself, and the antifouling method that uses electrical current that is generated by the fluid flow are disclosed. The composite material can be applied to medical devices, biomedical devices, industrial equipment, ship's hulls, food processing equipment, food processors, drinking water distribution systems, and home electrical appliances.

The FI-EMF consist of electroactive biopolymers and magnetic particles. This antifouling composite agent utilizes a fluorinated version of polycardanol in addition to magnetic particles to generate a coating that is capable of preventing biofilm formation. The base material is cardanol, a natural phenolic compound that has antifouling effects already. Cardanol is a major phenolic compound (80%) in cashew nut shell liquid (CNSL). Soybean peroxidase enzyme is used to polymerize cardanol to polycardanol. 2-(perfluorohexyl) ethyl methacrylate (FHEM) and methyl ethyl ketone peroxide (MEKP) are added to fluorinate and cross-link the polymers, respectively. Fluorinated polycardanol is cured on glass slides and metal surfaces. Fluorinated polycardanol showed excellent antifouling activity against sea creatures in experiments done in seawater.

In the preferred embodiment, the concentration of cross-linking catalyst, Cobalt Naphthenate, to be added into polycardanol is 0.3 wt %, and the oxidant, Methyl Ethyl Ketone Peroxide (MEKP), for curing should be also added at the same time at 1.0 wt %.

In the preferred embodiment, the fluorinated polycardanol coating is produced as follows: Cardanol is polymerized (as disclosed above) to create Polycardanol. 1 wt % fluoride compound is added, along with cobalt naphthenate (0.3 wt %)+MEKP (1.0 wt %) to make the fluorinated polycardanol coating. The mixture is applied to a solid surface and cured in the air for 24 hours.

While the preferred embodiment utilizes a Fluoride concentration of 1 wt % a concentration range of 0.1-10 wt % may be used, however, the preferred range is 1-3 wt %.

To increase its negative surface charge and electrical current, magnetic particles (such as strontium ferrite, 2 μm) are added to the polycardanol coating. Electrical current is generated when an electrolyte liquid such as water, urine, or blood, flows over the polycardanol/ferrite composite coating.

In the preferred embodiment, the fluorinated ferrite polycardanol coating is produced as follows: Cardanol is polymerized (as disclosed above) to create Polycardanol. 1 wt % fluoride compound is added along with cobalt naphthenate (0.3 wt %)+MEKP (1.0 wt %)+Ferrite (10 wt %) to make the fluorinated ferrite polycardanol coating. The mixture is applied to a solid surface and cured in the air for 24 hours.

While the preferred embodiment utilizes a Ferrite concentration range of 10 wt %, a concentration range of 0.1-25 wt % may be used, however, the preferred range is 5-15 wt %.

Figure 5:
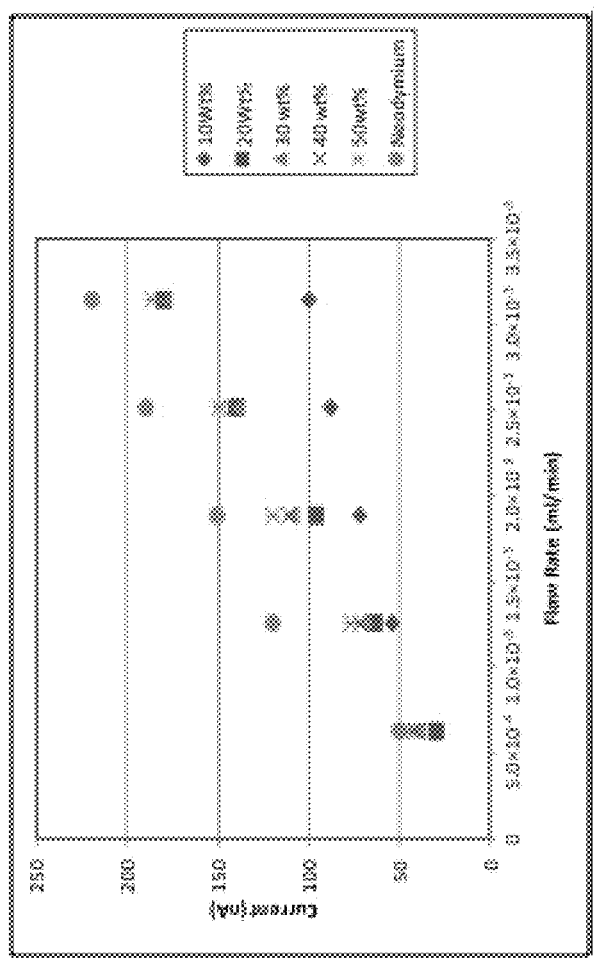
FIG. 5 is a graph showing the current generated as flow rate and magnetic content increase.

The use of "flow-induced electricity" generated through magnetic particles is a novel approach aimed at adding to the antifouling characteristics of polycardanol. Referring now to FIG. 5, an experiment investigating the impact of magnetic particle density within the composite coating at generating electromagnetic force, an average current of 185 nA was generated. The current was linearly proportional to the density of ferrite and the flow rate of synthetic urine.

Figure 4:
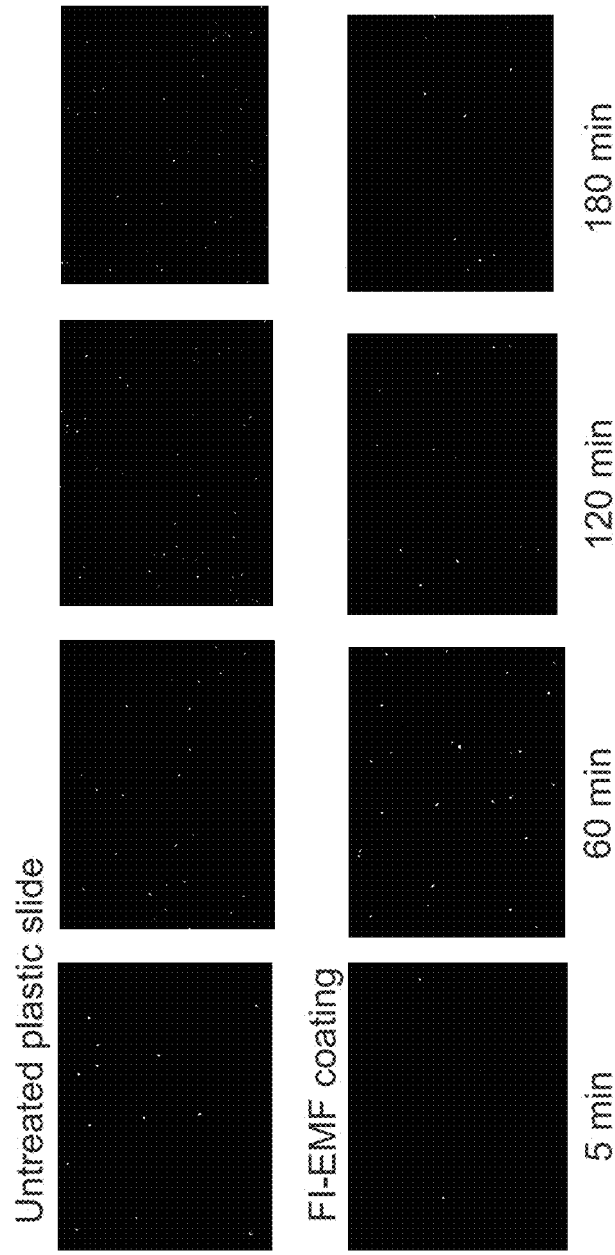
FIG. 4 are slides depicting the images of bacterial cells (*E. coli*, ATCC 11775, genetically modified with red fluorescent protein (RFP)) attached to (a) a regular glass surface and (b) a glass surface coated with the antifouling composite agent.

Referring now to FIG. 4, to test the antifouling effect of the composite coating (fluorinated polycardanol and ferrite particles, named FI-EMF coating), experiments were performed using *E. coli* expressing pDsRed (ATCC 11775) in a flow cell model. In this model, red fluorescent bacteria were added to synthetic urine and circulated over a coated plastic slide for three hours. In a control experiment, fluorescent bacteria were circulated over an uncoated slide. The images of the cells attached to the surface were taken using a fluorescent microscope installed over the flow-cell chamber. Herein, were found a 70% reduction in bacteria attachment on slides treated with composite FI-EMF coating as compared to non-coated slide. The FI-EMF composite coating demonstrated a significant increase in an ability to prevent bacteria attachment over a three-hour period as compared to polycardanol coated slides.

Hydrophilicity of the FI-EMF coating was measured and compared with a leading antifouling brand SigmaGlide™ (PPG Industries). As shown in Table 1, with 1 wt % fluorination, the fluorinated polycardanol showed a contact angle of 114° where SigmaGlide™ coating showed 105°. The FI-EMF proved to be a better surface energy lowering agent capable of further reducing bacterial and protein attachment as compared to SigmaGlide™. Adhesive force, an indicator of surface stickiness, was measured using a wood block (1-cm diameter) glued to the coatings by an epoxy adhesive. A force of 0.2 Kg/cm² was required for the 1 wt % FI-EMF coating. 0.4 Kg/cm² force was required for SigmaGlide™, a commercially available antifouling compound. The table below shows the FI-EMF versus SigmaGlide. The contact angles and adhesions force was tested. A greater contact angle indicates surface energy reduction. Conversely, a lower adhesion force results in less fouling agent attachment. The adhesion force depicts the force required to detach a wood block (1 cm diameter) that has been glued on the coating by an epoxy adhesive.

| Weight % of fluoride in polycaradanol coating | Contact angle (°) (Goniometer) | Adhesion force* (Kg/cm²) |
|---|---|---|
| 0 | 75 | >5 |
| 0.1 | 85 | 4 |
| 0.5 | 92 | 3.1 |
| 1 | 114 | 0.2 |
| 3 | 110 | 0.4 |
| 5 | 91 | 3.5 |
| 10 | 87 | 4.5 |
| SigmaGlide | 105 | 0.4 |

Biofouling is a process that forms layers of bacteria and their metabolites such as biopolymers and proteins during bacterial colonization of a solid surface. Usually biofouling causes serious damages in industry, medical, and public health areas. Bacterial colonization and growth inside pipelines in industry causes or facilitates corrosion of pipes, reduces heat-transfer efficiency, and increases energy costs for pump operation. In medical field, biofouling on the urinary and blood vessel catheters is the cause of catheter-induced infection. Proteins and mineral accumulation on stents causes problems in blood circulation. Effective prevention of biofilm formation is extremely important for human health and successful industrial operation. For the antifouling agents that have been identified and studied, their antifouling effect is thought to be caused by a combination of several mechanisms. One of them is the surface charge of the antifouling coatings. Due to the negatively charged bacterial cells, a negatively charged coating surface repels bacteria, which results in less bacterial attachment on the coated surface. To facilitate this mechanism, coating agent has been developed that enhances the surface charge effect. The FI-EMF coating is based on the Faraday's law of induction that states the voltage induced across any conductor as it moves at right angles through a magnetic field is proportional to the velocity of that conductor. Due to this voltage created on the surface of the coating agent, bacterial cells are repelled from the surface of the wall. Magnetic field is generated by the coating material itself. The coating material consists of a newly developed ferrite-polycardanol composite. Polycardanol itself already has been verified to have antifouling activity. Preliminary tests show the ferrite-cardanol composite has enhanced antifouling effect. The main component of the FI-EMF is the ferrite-polycardanol composite material. The composite consists of ferrite particles and cardanol polymerized and cross-linked by enzymatic polymerization method. Cardanol is a liquid byproduct obtained from cashew nut shells. It is regarded as a renewable waste abundantly produced in cashew nut producing countries such as India, Vietnam and Mozambique. Currently cardanol is used as an alternative to petroleum-based phenol for manufacturing brake linings in car manufacturing industry and construction materials in construction materials industry in the United States and many other countries. By adding magnetic materials such as ferrite into the polymer coating electrical voltage is generated by the flow of the liquid. This flow-induced voltage acts like an electric zap on bacteria near the pipe wall and prevents them from adhesion.

FI-EMF antifouling technology may be used in many applications. The urinary catheter market is huge and it is growing very fast. Especially in Europe and North America, its demand is increasing sharply because of the growing old as population. Recently the use of urinary catheter for long-term care patients has increased dramatically in the United States. Marine application is another market where FI-EMF would be useful. Because of the attachment of sea creatures such as barnacles and shells, a ship must use 30% more fuel to sail due to the increased friction. Organic tin has been used for ship painting, but it was banned by Maritime Organization due to its negative environmental impact. FI-EMF is a great alternative when applied to a ship's hull. FI-EMF can be used in food processing equipment, and the water container in a humidifier. The condenser unit in an air conditioner is known as a source of bacterial contamination. It is a source of air born bacteria and negatively affects human health. Our material can be used to prevent it.

FI-EMF technology is expected to be effective for prevention of protein adhesion to clinical and medical device surfaces. Catheter related blood stream infections (CRBSI) resulting from infected central venous catheters (CVC) result in approximately 28,000 deaths and add nearly $2.3 billion in preventable costs to the healthcare system. Thrombosis associated with peripherally inserted central catheters (PICC) is estimated to increase average hospital stays by 4.6 days and add $15,973 per incident. Protein adhesion on left ventricular assist devices (LVAD) causes serious problems in health-care industry, and should be prevented. Previous studies performed in our laboratory have demonstrated an ability of fluorinated coatings at preventing protein deposition of albumin and fibrinogen on coated surfaces as explained above.

Figure 6:
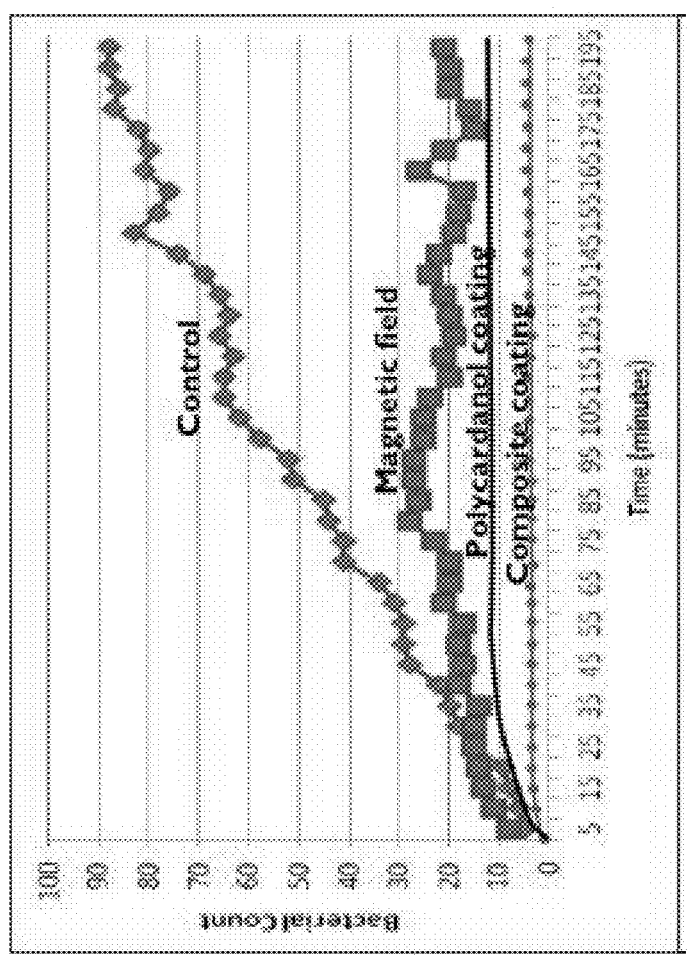
FIG. 6 is a graph showing the number of attached bacterial cells over time.
Figure 7:
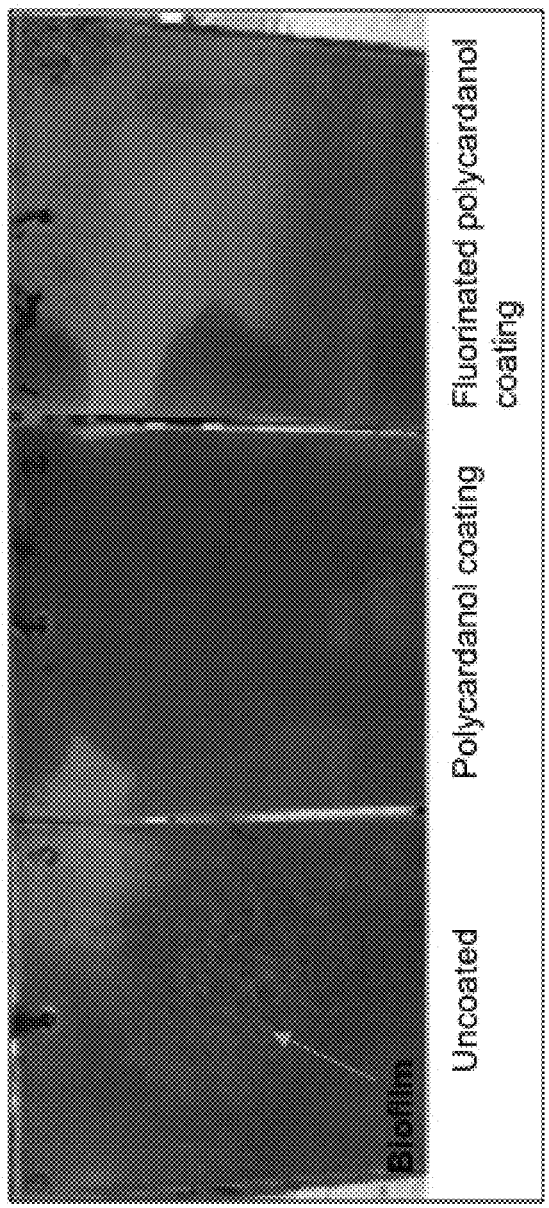
FIG. 7 shows the present invention applied to a solid surface and exposed to water over 2 months, versus an uncoated surface.

Referring now to FIG. 6, test results are shown to illustrate the antifouling capabilities of the FI-EMF (composite coating), versus the polycardanol coating and no coating. The FI-EMF displayed superior results over the true period. As shown in FIG. 7, three solid surfaces were exposed to water for two months. One surface was not coated with any antifouling agent; one surface was coated with polycardanol, while the last surface was coated with fluorinated polycardanol. Biofilm can be clearly seen on the untreated surface while the two treated surface repelled biofilm (algae).

While the preferred embodiment of the invention contains ferrite, any magnetic material may be used. Ferrite offers a low cost magnetic effect but is not intended to be the only embodiment. Similarly, a CNSL is used to obtain cardanol, but cardanol naturally occurs in a number of other compounds. It intended that cardanol may be obtained from any appropriate source.

In another embodiment of the invention, only the fluorinated polycardanol used as an antifouling agent. In this embodiment, no magnetic material is added the compound. This embodiment may be preferred for medical applications.

It should be noted that the FI-EMF requires a liquid flow for optimal effectiveness, it is anticipated that the liquid flow could be induced such as in a docked marine setting. A propulsion device could be used to create and artificial flow of liquid over the FI-EMF.

Example 1

Cashew nut shell liquid (CNSL) was tested as a model electroactive biopolymer. It demonstrated excellent antifouling activity when it was polymerized and cross-linked on a glass or a plastic surface.

Polyaniline was tested as a model conducting biopolymer. It demonstrated excellent conductivity when coated on either a glass or plastic surface in the range of $2\times10^{-1}$-$2\times10^{-3}$ S/cm.

The antifouling composite agent disclosed herein was tested for its conductivity and antifouling effects. When there was a flow of electrolyte that has the total ionic strength of 0.1165 mol/L at 2 ml/min, the conductivity was measured in the range of 0.5-250 Amp/meter depending on the concentration of magnetic particles in the coating. The electrolyte was synthesized by adding 54 g of sodium phosphate, 0.88 g of potassium di-basic phosphate, 2.52 g/L and 3.21 g/L of sodium chloride and potassium chloride, respectively to the phosphate buffer.

Example 2

The electroactive polymer and magnetic particle composite can be prepared as follows:
Enzymatic Polymerization of Antifouling Polymer (Polycardanol)
Materials: Cardanol (Cashew Nut Shell Liquid)
  Soybean peroxidase (SBP, Enzyme)
  Methanol
  Phosphate butter
  Hydrogen peroxide
  Methyl ethyl ketone peroxide
  Cobalt naphthenate
Method:
a. Prepare pH 7 phosphate buffer solution, 50 ml.
b. Prepare 30% $H_2O_2$ solution.
c. In a separate 500 ml beaker, mix 10 mg or soybean peroxidase (SBP) in an equivolume mixture of 12.5 ml of methanol and the phosphate buffer.
d. Add 300 mg of cardanol into the SBP solution prepared above. Continuously stir the solution with a magnetic bar.
e. Start adding $H_2O_2$ at 50 mL/hr for 3 hours using an infusion pump (syringe pump).
f. Let it sit for 24 hours.
g. Centrifuge the solution to precipitate the polymer in the bottom of a centrifuge tube.
h. Wash the polymer with methanol and water and centrifuge twice.
Synthesis of Polycardanol-Ferrite Composite Coating
1. Materials: Polycardanol polymer prepared in the section above
  Strontium ferrite ($SrFe_{12}O_{19}$) with the average particle size 1-1.5 μm
  Isopropyl-trisostearyl-titanate
  Ball Mill
  Methyl ethyl ketone peroxide (MEKP)
  Cobalt naphthenate Certain embodiments of the biofouling agent disclosed herein are defined in the examples herein. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:
1. An antifouling composite material that prevents liquid phase fouling agents from attaching to the solid surface, by generating electrical current using a polycardanol polymer, cross-linked, fluorinated, and integrated with magnetic par- ticles wherein the composite material generates electrical current when an electrolyte flows over the composite material.

2. The composite material of claim 1 wherein bacterial cells virus cells and protein molecules in a liquid phase are repelled by the electrical current which is generated by the flow of an electrolytic liquid over the composite material.

3. The composite material of claim 1 wherein the magnetic particles are strontium ferrite.

4. The composite material of claim 1 wherein chemical corrosion is prevented by the electrical current which is generated by the flow of an electrolytic liquid over the composite material.

5. The composite material of claim 1 wherein at least one surface of a medical instrument selected from the group consisting of: stents, LVAD, PICC, endoscopic imaging devices, harvesting devices, retractors, bone hooks, skin hooks, nerve hooks, tension devices, forceps, elevators, drill sleeves, osteotomes, spinal rongeurs, spreaders, gouges, bone files and rasps, bone awls, rib shears, trephines, suction tubes, taps, tamps, calipers, countersinks, suture passers, and probes has a layer of the composite material.

6. The composite material of claim 1 wherein the surface of biomedical materials and devices such as urinary catheters, artificial blood vessels, artificial organs, scaffolds for artificial bone and tissue have a layer of the composite material.

7. The composite material of claim 1 wherein the surface of ship's hulls, food processing equipment, food containers, drinking water distribution systems, and electrical appliances have a layer of the composite material.

8. An antifouling composite material comprising:
a polycardanol component, a fluoride component; and
a magnetic material.

9. The antifouling agent of claim 8 wherein the magnetic material is 5-15 wt %.

10. The antifouling agent of claim 9 wherein the magnetic material is 10 wt %.

11. The antifouling agent of claim 8 wherein the magnetic material is Ferrite.

12. The antifouling agent of claim 11 wherein the Ferrite is between 5-15 wt %.

13. The antifouling agent of claim 11 wherein the Ferrite is 10 wt %.

14. The antifouling agent of claim 8 wherein the fluoride component is 0.1-10 wt %.

15. The antifouling agent of claim 14 wherein the fluoride component is 1 wt %.

\* \* \* \* \*